(12) United States Patent
Bara

(10) Patent No.: US 6,184,277 B1
(45) Date of Patent: *Feb. 6, 2001

(54) COMPOSITION COMPRISING AN ORGANOPOLYSILOXANE GEL

(75) Inventor: Isabelle Bara, Paris (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/994,433

(22) Filed: Dec. 19, 1997

(30) Foreign Application Priority Data

Dec. 24, 1996 (FR) .................................................. 96 15986

(51) Int. Cl.[7] ................................ C08K 5/54; A61K 7/02
(52) U.S. Cl. ........................... 524/268; 424/401; 424/59; 424/63; 424/64
(58) Field of Search ................................ 424/401, 59, 63, 424/64; 524/268

(56) References Cited

U.S. PATENT DOCUMENTS

| | | | |
|---|---|---|---|
| 5,266,321 | * 11/1993 | Shukuzaki et al. | 424/401 |
| 5,736,125 | * 4/1998 | Morawsky et al. | 424/59 |
| 5,849,316 | * 12/1998 | Mellul et al. | 424/401 |
| 5,919,468 | * 7/1999 | Bara | 424/401 |
| 5,972,318 | * 10/1999 | Bara | 424/64 |
| 6,083,900 | * 7/2000 | Auguste et al. | 512/2 |

FOREIGN PATENT DOCUMENTS 0 610 014    8/1994   (EP) .

OTHER PUBLICATIONS

Chemical Abstracts, vol. 124, No. 8, Abstract No. 97276 (1996).

* cited by examiner

*Primary Examiner*—Margaret G. Moore
(74) *Attorney, Agent, or Firm*—Finnegan, Henderson, Farabow, Garrett & Dunner, L.L.P.

(57) ABSTRACT

A care composition containing, as gelling agent, at least one partially crosslinked, elastomeric solid organopolysiloxane combined with a fatty phase containing at least one polar oil and at least one cosolvent with a silicone structure comprising a chain which is pendent and/or at the end of a silicone structure, this chain being linear or branched and containing from 3 to 12 carbon atoms. This cosolvent is in particular volatile at ambient temperature, imparting coolness when applied.

22 Claims, No Drawings

COMPOSITION COMPRISING AN ORGANOPOLYSILOXANE GEL

The technology involved in this application is related to that disclosed in the following co-pending U.S. applications, filed on even date herewith:
(1) Title: Transfer-free Make-up or Care Composition Containing an Organopolysiloxane and a Fatty Phase
Inventors: Isabelle Bara and Frederic Auguste application Ser. No. 08/994,435
(2) Title: Non-migrating Make-up or Care Composition Containing an Organopolysiloxane and a Fatty Phase
Inventors: Isabelle BARA and Frederic AUGUSTE application Ser. No. 08/994,989

The specifications of these related applications are hereby specifically incorporated by reference.

The present invention relates to a composition for the care and/or treatment of the skin, including the scalp, and/or the lips of human beings, containing an organopolysiloxane gel as gelling agent. This composition can be employed in the cosmetics or dermatological field. More particularly, this composition is in the form of a homogeneous anhydrous gel containing one or more treating oils. In particular, this composition allows the hydration and the nutrition of the skin, providing it with suppleness and softness.

Anhydrous gels based on crosslinked elastomeric organosiloxane, as described in U.S. Pat. No. 4,789,169, are known to be products intended to be applied to the skin, exhibiting good cosmetic properties like softness, a matte appearance and a nongreasy feel.

Most homogeneous gels are obtained by swelling resins with oils of silicone character, such as linear polydimethylsiloxanes (PDMS) and cyclomethicones, or nonpolar oils such as volatile or nonvolatile derivatives of paraffin originating from petroleum oil, or synthetic ones such as perhydrosqualane.

Although they impart some properties to the skin (antidehydrating property via a protective action or by opposing imperceptible loss of water—ILW), these oils are not in any case "treating" the skin. This is because care oils are of vegetable origin and polar in nature, such as triglycerides.

Unfortunately, these polar oils are capable of being gelled with elastomeric silicones only with very great difficulty; the mixture is either unfeasible or, if it does form, is unstable with the passage of time and granular and opaque in appearance. In addition, when employed as they are, these oils are too fluid to be easily applied to the skin. Furthermore, they give the skin a greasy feel, which is not very comfortable, and a shiny appearance.

The subject-matter of the invention is a composition for the care and/or treatment of the skin and/or of the lips enabling these disadvantages to be overcome. Surprisingly, it has been found that the use of fluid alkyldimethicone, also called silicone oil with an alkyl chain, allows the polar treating oils to be made compatible with organopolysiloxane resins and to produce translucent, even transparent, stable gels enabling the treating oils to be conveyed without restriction and in a pleasant manner.

The invention applies not only to the products for the care and/or treatment of the skin, including the scalp and the mucosae such as the lips and the inside of the eyelids, but also to lip make-up products which have care and/or treatment properties, and to make-up products for the skin, both of the face and of the body, which have a care and/or treating function.

More precisely, the subject-matter of the invention is a composition containing at least one partially crosslinked elastomeric solid organopolysiloxane as gelling agent, associated with a fatty phase containing at least one polar oil and at least one cosolvent with a silicone structure comprising at least one alkyl chain which is pendent and/or at the end of a silicone structure, this chain being linear or branched and containing from 3 to 12 carbon atoms.

This composition can be employed as it is or else can be incorporated into a more complex composition.

"Elastomeric" is intended to mean a deformable, flexible material which has viscoelastic properties and which exhibits especially the consistency of a sponge or of a flexible sphere.

The elastomeric organopolysiloxanes of the composition according to the invention have a remarkable oil-gelling power. They are not desiccant to the skin and contribute good cosmetic properties. These new elastomers produce compositions which are comfortable to apply, soft and which do not feel sticky. This softness is due especially to the texture of the organopolysiloxanes.

In addition, by virtue of the presence of polar oil, these compositions have treating and/or care properties.

The composition of the invention may take the form of paste, solid or cream. It may be an oil-in-water or water-in-oil emulsion or a solid or flexible anhydrous gel. It preferably takes the form of translucent or transparent anhydrous gel.

The cosolvent(s) is/are advantageously volatile oils, that is to say oils capable of evaporating at ambient temperature, especially from the skin and/or the lips. In this case, after evaporation of the volatile oil or oils, the compositions of the invention produce a homogeneous and uniform film which has a texture that is light and imparting coolness, this being despite the presence of two initially incompatible materials.

The elastomeric organopolysiloxanes of the composition according to the invention are in general partially or completely crosslinked and three-dimensional in structure. When included in a fatty phase, they are transformed, depending on the fatty phase content employed, from a product of spongy appearance when they are employed in the presence of low contents of fatty phase, to a more or less homogeneous gel, in the presence of larger quantities of fatty phase. The gelling of the fatty phase by these elastomers may be complete or partial.

The elastomers of the composition of the invention are generally conveyed in the form of gel comprising an elastomeric organopolysiloxane of three-dimensional structure, included in at least one hydrocarbon oil and/or a silicone oil.

The elastomeric organopolysiloxanes of the composition according to the invention may be selected from the crosslinked polymers described in European application EP-A-0 295 886, the disclosure of which is specifically incorporated by reference herein. According to EP-A-0 295 886, these organopolysiloxanes are obtained by an addition and crosslinking reaction, in the presence of a catalyst of the platinum type, of at least:
(a) an organopolysiloxane containing at least two $C_2$–$C_6$ lower alkenyl groups per molecule; and
(b) an organopolysiloxane containing at least two hydrogen atoms bonded to a silicon atom per molecule.

The elastomeric organopolysiloxanes of the composition according to the invention may also be chosen from those described in U.S. Pat. No. 5,266,321, the disclosure of which is specifically incorporated by reference herein. According to this patent, the organopolysiloxanes are selected especially from:
i) the organopolysiloxanes including $R_2SiO$ and $RSiO_{1.5}$ units and optionally $R_3SiO_{0.5}$ and/or $SiO_2$ units in which the radicals R, independently of one another, denote a hydrogen, an alkyl such as methyl, ethyl or propyl, an aryl such as phenyl or tolyl or an unsaturated aliphatic group such as vinyl, the weight ratio of the $R_2SiO$ units to the $RSiO_5$, units ranging from 1/1 to 30/1;

ii) the organopolysiloxanes which are insoluble and swellable in a silicone oil, obtained by addition of an organohydropolysiloxane (1) and of an organopolysiloxane (2) containing unsaturated aliphatic groups, such that the quantity of hydrogen or of unsaturated aliphatic groups in (1) and (2) respectively ranges from 1 to 20 mol % when the organopolysiloxane is noncyclic and from 1 to 50 mol % when the organopolysiloxane is cyclic.

The organopolysiloxanes which are the subject-matter of the invention are, for example, those marketed under the names KSG6 by Shin-Etsu, TREFIL E-505C or TREFIL E-506C by Dow-Corning, GRANSIL by Grant Industries (SR-CYC, SR DMF10, SR-DC556), or those marketed in the form of gels already formed (KSG15, K5G17, KSG16, K5G18 by Shin-Etsu, GRANSIL SR 5CYC gel, GRANSIL SR DMF 10 gel, GRANSIL SR DC 556 gel, SF 1204 and JK 113 by General Electric. A mixture of these commercial products may also be employed.

The organopolysiloxane(s) is/are preferably present, as active substance, in a concentration preferably ranging from 0.1 to 80% of the total weight of the composition, and more preferably from 2 to 60%.

The volatile silicones containing an alkyl chain preferably correspond to the following formula (1):

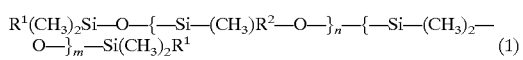

$$R^1(CH_3)_2Si\text{—}O\text{—}\{\text{—}Si\text{—}(CH_3)R^2\text{—}O\text{—}\}_n\text{—}\{\text{—}Si\text{—}(CH_3)_2\text{—}O\text{—}\}_m\text{—}Si(CH_3)_2R^1 \quad (1)$$

in which:

$R^1$ and $R^2$ independently represent hydrogen, methyl or a linear or branched alkyl chain containing from 3 to 10 carbon atoms, n and m represent integers ranging from 0 to 10, on condition that if $R^1$ is H or methyl, n is not 0 and $R^2$ denotes an alkyl chain of from 3 to 10 atoms.

The volatile silicones of formula (1) preferably have a molecular mass ranging from 290 to 3000 and a volatility or evaporation rate Nv generally ranging from 150 to 500 seconds (time corresponding to the evaporation of 0.2 ml of volatile silicone at 23° C. in a stable atmosphere at 50% relative humidity).

As volatile alkylsilicones which can be employed in the invention there may be mentioned the alkylheptamethyltrisiloxanes with a $C_4$, $C_5$, $C_6$, $C_7$ and $C_8$ alkyl group like, for example, hexylheptamethyltrisiloxane of formula: $(CH_3)_3$—Si—O—Si$(CH_3)(C_6H_{13})$—O—Si$(CH_3)_3$; octylheptamethyltrisiloxane of formula: $(CH_3)_3$—Si—O—Si$(CH_3)$$(C_8H_{15})$—O—Si$(CH_3)_3$; and mixtures thereof.

The alkylated volatile silicone oil or oils preferably represent from 10 to 99% by weight relative to the polar oils and, more preferably, from 20% to 80%.

The use of a cosolvent according to the invention allows the elastomeric organopolysiloxane to be made compatible with the polar oils. In addition, the use of a volatile cosolvent has the advantage of rapid elimination, leaving behind only the organopolysiloxane and the polar oil on the region of application of the composition.

As polar oils which can be employed in the invention there may be mentioned especially:

vegetable hydrocarbon oils such as the liquid triglycerides of fatty acids, the triglycerides of caprylic/capric acids like those sold by the company Stearineries Dubois or those sold under the names MIGLYOL 810, 812 and 818 by the company Dynamit Nobel;

the oils of formula $R_9COOR_{10}$ in which $R_9$ denotes the residue of a higher fatty acid containing from 7 to 19 carbon atoms, and $R_{10}$ denotes a branched hydrocarbon chain containing from 3 to 20 carbon atoms, like, for example, Purcellin oil (cetostearyl octanoate);

synthetic esters and ethers like isopropyl myristate and alcohol or polyalcohol octanoates, decanoates or ricinoleates;

fatty alcohols like octyldodecanol or oleyl alcohol;

mixtures thereof.

The polar oils of the invention are preferably hydrocarbon vegetable oils with a high content of triglycerides comprising esters of fatty acids and glycerol in which the fatty acids may have varied chain lengths, it being possible for the latter to be linear or branched, saturated or unsaturated; these oils are especially wheat germ, corn, sunflower, shea, castor, sweet almond, macadamia, apricot, soya, cotton, lucerne, poppy, pumpkin, sesame, marrow, avocado, hazelnut, grape or blackcurrant seed, evening primrose, millet, barley, quinoa, olive, rye, safflower, candlenut, passionflower and muscat rose oil. These vegetable oils have the special property of being liquid at a temperature equal to or lower than 25° C.

To the polar oils may be optionally added nonpolar or apolar oils like silicone oils such as linear or cyclic, volatile or nonvolatile polymethylsiloxanes which are liquid or pasty at ambient temperature, linear or branched hydrocarbons of synthetic or mineral origin, like volatile or nonvolatile liquid paraffins and their derivatives, liquid petrolatum, polydecenes and hydrogenated polyisobutene such as parleam.

The polar oils preferably represent from 0.2 to 80% of the total weight of the composition, more preferably from 1 to 50%. The nonpolar or apolar oils preferably represent from 0 to 80% of the weight of the composition and, more preferably, from 0 to 30%.

The composition of the invention may additionally include any additive usually employed in the field in question, such as water, water-soluble or liposoluble dyes, antioxidants, essential oils, preserving agents, neutralizing agents, liposoluble polymers, especially hydrocarbons such as polyalkylenes, cosmetic or dermatological active agents like, for example, emollients, hydrating agents, vitamins, antiwrinkle agents, essentially fatty acids, lipophilic sunscreens and gelling agents for the aqueous phase. These additives may be present in the composition preferably in a proportion of 0 to 20% of the total weight of the composition and, more preferably, of 0 to 10%.

A person skilled in the art will, of course, take care to choose the possible supplementary additives and/or their quantity so that the advantageous properties of the composition according to the invention are not, or are not substantially, damaged by the envisaged addition.

The composition according to the invention advantageously takes the form of an anhydrous gel which may be translucent or even transparent.

The composition according to the invention may take the form of a dermatological or skin care composition, or the form of a solar protection or make-up removal composition. In these various forms, it may be colorless, optionally containing cosmetic or dermatological active agents. It may then be employed as a care base for the skin or the lips (lip salves, protecting the lips from the cold and/or from the sun and/or from the wind).

The composition of the invention may also take the form of a colored product for making up the skin, in particular a foundation, a blush, a blusher or an eyeshadow, or for making up the lips, such as a lip-rouge exhibiting care or treatment properties.

The composition of the invention must, of course, be cosmetically or dermatologically acceptable, namely non-toxic and capable of being applied to the skin or to the mucosae (e.g. lips, interior of the eyelids) of human beings.

The composition of the invention may include a particulate phase, generally present in a proportion preferably ranging from 0 to 35% of the total weight of the composition, more preferably of 5 to 25%, and which may include pigments and/or mothers-of-pearl and/or fillers usually employed in cosmetic compositions.

The composition according to the invention may be manufactured by the known processes generally employed in the cosmetics or dermatological field.

Another subject-matter of the invention is a cosmetic process for care or treatment of the skin or of the mucosae of human beings, including the application of the composition as defined above to the skin or the mucosae.

The invention is illustrated in further detail in the following examples. The examples are in no way limiting. The percentages given are by weight.

EXAMPLE 1

Face Care Oil

| | |
|---|---|
| Sunflower oil | 5.00% |
| Muscat rose oil | 0.87% |
| Blackcurrant seed oil | 0.45% |
| Antioxidant | 0.03% |
| n-Hexylheptamethyltrisiloxane sold by Dow Corning under the name of DC1731 | q.s. 100% |
| Mixture of 40% by weight of polydimethylsiloxane 6 cst and of 60% by weight of partially crosslinked polydimethyl organosiloxane sold under the name KSG6 by Shin Etsu | 50.00% |

Preparation: The organopolysiloxane was swollen in the mixture of volatile and polar oils at ambient temperature in the presence of the antioxidant.

A translucent and colorless anhydrous gel, with a pleasant texture was obtained, which spread well and homogeneously.

EXAMPLE 2

Gelled Dispersion for Face Skin Care

| | |
|---|---|
| Elastomeric organopolysiloxane (KSG6) | 10.00% |
| PERMULEN TR2 from Goodrich (acrylates/$C_{10}$–$C_{30}$ alkyl acrylate crosspolymer - dispersant -) | 0.10% |
| CARBOPOL 980 from Goodrich (carboxyvinyl - gelling agent for aqueous phase -) | 0.60% |
| Triethanolamine (neutralizing agent) | 0.80% |
| Preserving agent | q.s. |
| n-Hexylheptamethyltrisiloxane sold by Dow Corning under the name of DC1731 | 10.00% |
| Apricot oil | 10.00% |
| Antioxidant | 0.03% |
| Water | q.s. 100% |

What is claimed is:

1. A composition comprising, as a gelling agent, at least one elastomeric, solid, and at least partially crosslinked organopolysiloxane and further comprising a fatty phase containing at least one polar oil and at least one cosolvent with a silicone structure, wherein said at least one cosolvent comprises at least one alkyl chain which is pendent and/or at the end of a silicone structure, said at least one alkyl chain being linear or branched and containing from 3 to 12 carbon atoms, wherein said composition is translucent.

2. A composition according to claim 1, wherein said at least one cosolvent is a volatile oil.

3. A composition according to claim 1, wherein said at least one cosolvent has the following formula (1):

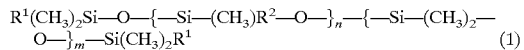

in which:
  $R^1$ and $R^2$ independently represent hydrogen, methyl or a linear or branched alkyl chain containing from 3 to 10 carbon atoms,
n and m represent integers ranging from 0 to 10,
wherein if $R^1$ is H or methyl, n is not 0 and $R^2$ denotes an alkyl chain of from 3 to 10 atoms.

4. A composition according to claim 3, wherein said at least one cosolvent is selected from hexylheptamethyltrisiloxane and octylheptamethyltrisiloxane.

5. A composition according to claim 1, wherein said at least one cosolvent is present in a concentration ranging from 10 to 99% by weight relative to the total weight of said at least one polar oil.

6. A composition according to claim 5, wherein said at least one cosolvent is present in a concentration ranging from 20 to 80% by weight relative to the total weight of said at least one polar oil.

7. A composition according to claim 1, wherein said at least one polar oil is selected from:
  vegetable hydrocarbon oils;
  oils of formula $R_9COOR_{10}$ in which $R_9$ denotes the residue of a higher fatty acid containing from 7 to 19 carbon atoms, and $R_{10}$ denotes a branched hydrocarbon chain containing from 3 to 20 carbon atoms;
  synthetic esters, synthetic ethers, polyalcohol octanoates, decanoates and ricinoleates; and
  fatty alcohols.

8. A composition according to claim 1, wherein said at least one polar oil is a vegetable oil with a high content of triglycerides.

9. A composition according to claim 1, wherein said at least one polar oil is present in a concentration ranging from 0.2 to 80% by weight, relative to the total weight of said composition.

10. A composition according to claim 9, wherein said at least one polar oil is present in a concentration ranging from 1 to 50% by weight, relative to the total weight of said composition.

11. A composition according to claim 1, wherein said fatty phase further comprises at least one additional oil selected from nonpolar and apolar oils.

12. A composition according to claim 11, wherein said at least one additional oil is present in a concentration ranging up to 80% by weight, relative to the total weight of said composition.

13. A composition according to claim 1, wherein said at least one elastomeric solid organopolysiloxane is obtained by an addition and crosslinking reaction, in the presence of a catalyst, of at least:
  (a) an organopolysiloxane containing at least two $C_2$–$C_6$ lower alkenyl groups per molecule; and
  (b) an organopolysiloxane containing at least two hydrogen atoms bonded to a silicon atom per molecule.

14. A composition according to claim 1, wherein said elastomeric solid organopolysiloxane is selected from:
  (i) organopolysiloxanes including $R_2SiO$ and $RSiO_{1.5}$ units and optionally $R_3SiO_{0.5}$ and/or $SiO_2$ units in which the radicals R, independently of one another, denote a hydrogen, an alkyl, an aryl or an unsaturated aliphatic group and the weight ratio of the $R_2SiO$ units to the $RSiO_{1.5}$ units ranges from 1/1 to 30/1; and (ii) organopolysiloxanes which are insoluble in silicone oil, obtained by addition of an organohydropolysiloxane and of an organo-polysiloxane containing unsaturated aliphatic groups, such that the quantity of hydrogen or of unsaturated aliphatic groups in said organohydropolysiloxane and said organopolysiloxane, respectively, ranges from 1 to 20 mol % when the organopolysiloxane is noncyclic and from 1 to 50 mol % when the organopolysiloxane is cyclic.

15. A composition according to claim 1, wherein said elastomeric solid organopolysiloxane is present as an active substance in a concentration ranging from 0.1 to 80% by weight relative to the total weight of said composition.

16. A composition according to claim 15, wherein said elastomeric solid organopolysiloxane is present as an active substance in a concentration ranging from 2 to 60% by weight relative to the total weight of said composition.

17. A composition according to claim 1, wherein said composition is in the form of an oil-in-water emulsion, a water-in-oil emulsion, a paste, a solid, a cream or a flexible anhydrous gel.

18. A composition according to claim 1, wherein said composition further comprises at least one cosmetic or dermatological active agent.

19. A composition according to claim 1, wherein said composition additionally contains at least one non-polar oil and/or at least one additive selected from water, water-soluble and liposoluble dyes, antioxidants, essential oils, preserving agents, gelling agents for an aqueous phase, neutralizing agents and liposoluble polymers.

20. A product for the care and/or treatment of skin or mucosae, said product comprising a composition according to claim 1.

21. A make-up product for skin or mucosae, said make-up product having a care and/or treatment function and comprising a composition according to claim 1.

22. A process for caring and/or treating the skin or the mucosae of human beings comprising applying a cosmetic or dermatological composition according to claim 1 to said skin or mucosae.

* * * * *